United States Patent
Nakamura et al.

(10) Patent No.: US 12,310,557 B2
(45) Date of Patent: May 27, 2025

(54) FLEXIBLE TUBE INSERTION APPARATUS, CONTROL APPARATUS, AND METHOD OF CHANGING RIGIDITY

(71) Applicant: OLYMPUS CORPORATION, Tokyo (JP)

(72) Inventors: Shuji Nakamura, Akishima (JP); Takeshi Takahashi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 836 days.

(21) Appl. No.: 17/405,261

(22) Filed: Aug. 18, 2021

(65) Prior Publication Data

US 2021/0369084 A1 Dec. 2, 2021

Related U.S. Application Data

(63) Continuation of application No. PCT/JP2019/007384, filed on Feb. 26, 2019.

(51) Int. Cl.
*A61B 1/005* (2006.01)
*A61B 1/00* (2006.01)
*A61M 25/01* (2006.01)

(52) U.S. Cl.
CPC ........ *A61B 1/0052* (2013.01); *A61B 1/00006* (2013.01); *A61B 1/00078* (2013.01); *A61B 1/0058* (2013.01); *A61B 1/009* (2022.02); *A61M 25/0127* (2013.01); *A61M 25/0155* (2013.01)

(58) Field of Classification Search
CPC .......................... A61B 1/0058; A61M 25/0155
See application file for complete search history.

(56) References Cited

U.S. PATENT DOCUMENTS

| | | | | |
|---|---|---|---|---|
| 4,884,557 | A * | 12/1989 | Takehana | A61B 1/0058 600/145 |
| 2007/0043261 | A1* | 2/2007 | Watanabe | A61B 1/00071 600/152 |
| 2013/0150666 | A1* | 6/2013 | Otawara | A61B 1/00117 600/104 |
| 2015/0272425 | A1* | 10/2015 | Ueda | A61B 1/00078 600/144 |

(Continued)

FOREIGN PATENT DOCUMENTS

EP 1 757 218 A2 2/2007
EP 2 923 633 A1 9/2015

(Continued)

OTHER PUBLICATIONS

International Search Report dated May 28, 2019 received in PCT/JP2019/007384.
English abstract only of EP 3 128 168 A1.

*Primary Examiner* — Anh Tuan T Nguyen
*Assistant Examiner* — Jae Woo
(74) *Attorney, Agent, or Firm* — Scully, Scott, Murphy & Presser, P.C.

(57) ABSTRACT

A flexible tube insertion apparatus includes an insertion section inserted into an insertion target conduit, a rigidity variable member disposed inside the insertion section and capable of changing rigidity, and a binding member configured to bind a proximal end portion of the rigidity variable member to be capable of changing a pressing force applied to an outer circumferential surface of the proximal end portion.

6 Claims, 14 Drawing Sheets

(56) References Cited

U.S. PATENT DOCUMENTS

| | | | | |
|---|---|---|---|---|
| 2018/0028049 A1* | 2/2018 | Takahashi | ............ | A61B 1/0669 |
| 2018/0263467 A1* | 9/2018 | Takahashi | .............. | A61B 1/009 |
| 2018/0296798 A1* | 10/2018 | Lepak | ............... | A61M 25/0136 |
| 2018/0317751 A1* | 11/2018 | Kuboi | ................ | A61B 1/00006 |
| 2019/0046010 A1* | 2/2019 | Tojo | ..................... | A61B 1/0055 |
| 2019/0046011 A1* | 2/2019 | Ikeda | ................. | A61B 1/00078 |
| 2019/0374089 A1* | 12/2019 | Nakamura | ............. | A61B 1/009 |
| 2020/0037853 A1* | 2/2020 | Kitanaka | ............ | A61B 1/00078 |

FOREIGN PATENT DOCUMENTS

| | | |
|---|---|---|
| JP | 2003-070726 A | 3/2003 |
| JP | 2003-180622 A | 7/2003 |
| JP | 2007-054125 A | 3/2007 |
| JP | 2009-061173 A | 3/2009 |
| JP | 2015-188673 A | 11/2015 |
| JP | 2016-007434 A | 1/2016 |
| JP | 2017-507286 A | 3/2017 |

* cited by examiner

FLEXIBLE TUBE INSERTION APPARATUS, CONTROL APPARATUS, AND METHOD OF CHANGING RIGIDITY

CROSS REFERENCE TO RELATED APPLICATION

This application is a continuation application of PCT/JP2019/007384 filed on Feb. 26, 2019, the entire contents of which are incorporated herein by this reference.

BACKGROUND OF THE INVENTION

1. Field of the Invention

The present invention relates to a flexible tube insertion apparatus and relates to a flexible tube insertion apparatus in which a rigidity variable mechanism is provided inside an elongated insertion section having flexibility, a control apparatus, and a method of changing rigidity.

2. Description of the Related Art

There has been widely known a technique for inserting an elongated insertion section having flexibility to a deep part in a subject. For example, in a medical field, there has been widely known a technique for picking up an image of an object inside the subject using an endoscope including an elongated insertion section.

In general, the insertion section of the endoscope of this type is configured by disposing a distal end rigid portion, a bending portion, and a flexible portion (a flexible tube portion) in order from a distal end. When the endoscope insertion section is inserted into a body cavity, which is a subject, a surgeon bends the bending portion in a desired direction by operating an operation knob disposed in an operation section of the endoscope while gripping the flexible portion (the flexible tube portion) and pushing the insertion section into the body cavity.

It is assumed that, when the endoscope insertion section described above is inserted into the subject, the endoscope insertion section is further pushed into the subject in a state in which the bending portion or the flexible portion (the flexible tube portion) is bent. In this case, it is likely that an unreasonable load is applied to a body cavity wall of the subject depending on an amount of pushing-in force and the body cavity is extended more than necessary.

In view of such circumstances, there has been proposed a technique for improving insertion performance of the endoscope insertion section. For example, Japanese Patent Application Laid-Open Publication No. 2016-7434 describes a technique for dividing an insertion section into segments in a longitudinal direction, detecting a shape of each of the segments, and changing rigidity according to the shape to improve insertability.

Japanese Patent Application Laid-Open Publication No. 2003-180622 describes a technique in which a rigidity variable mechanism (a hardness variable mechanism) is included and which improves insertability of an insertion section by controlling the rigidity variable mechanism. The rigidity variable mechanism (the hardness variable mechanism) is formed by a wire for hardness change and a coil for hardness change. A distal end of the wire for hardness change is firmly fixed by brazing or the like. On the other hand, an end portion on a hand side is restricted from moving by a coil stopper.

SUMMARY OF THE INVENTION

A flexible tube insertion apparatus according to an aspect of the present invention includes: an insertion section inserted into an insertion target conduit; a rigidity variable member disposed inside the insertion section and capable of changing rigidity; and a binding member configured to bind a proximal end portion of the rigidity variable member to be capable of changing a pressing force applied to an outer circumferential surface of the proximal end portion.

A control apparatus according to an aspect of the present invention includes a processor configured by at least one piece of hardware. The processor calculates a bending direction of a bendable insertion section of an endoscope including the insertion section and determines, based on the calculated bending direction, a pressing force of a binding member applied to an outer circumferential surface of a proximal end portion of a rigidity variable member capable of changing rigidity, the binding member being provided on the outer circumferential surface.

A method of changing rigidity according to an aspect of the present invention is a method of changing rigidity of a rigidity variable member disposed inside an insertion section of an endoscope and capable of changing rigidity, the method including: calculating a bending direction of the insertion section; and changing, based on the calculated bending direction, a pressing force applied to an outer circumferential surface of a proximal end portion of the rigidity variable member.

DETAILED DESCRIPTION OF THE PREFERRED EMBODIMENTS

Embodiments of the present invention are explained below with reference to the drawings.

First Embodiment

Figure 1:
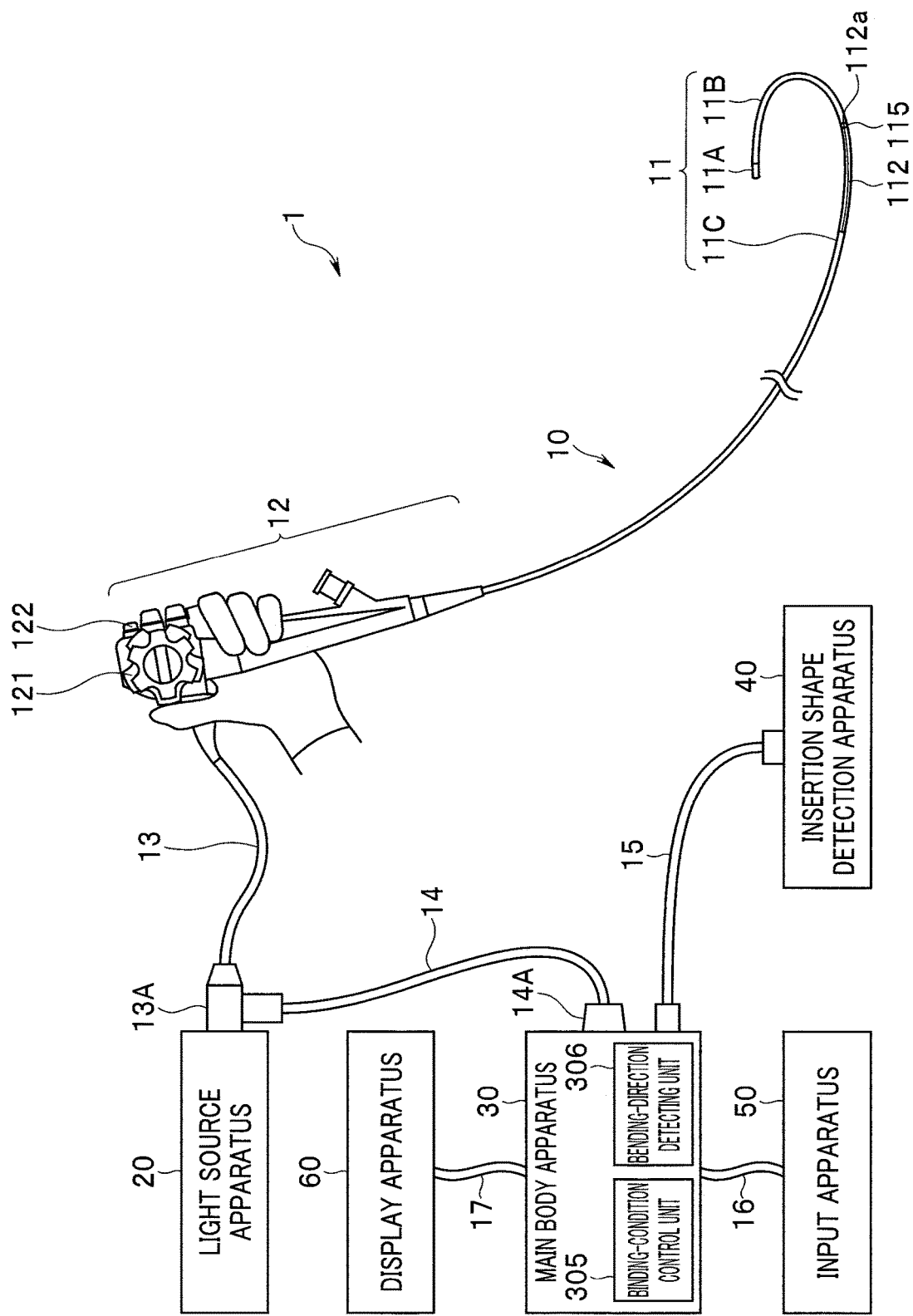
FIG. 1 is a block diagram showing a configuration of an endoscope system including a flexible tube insertion apparatus according to a first embodiment of the present invention.
Figure 2:
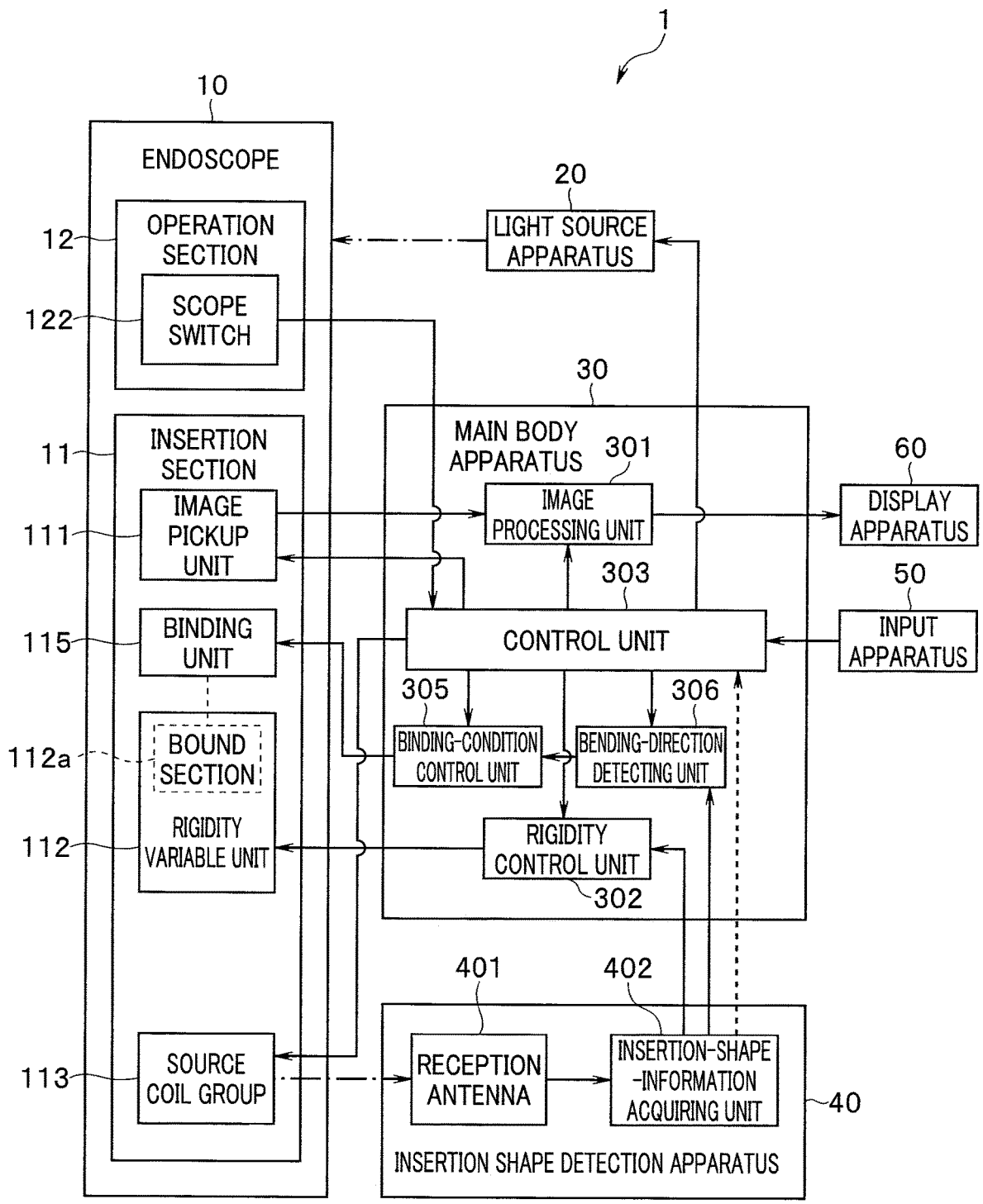
FIG. 2 is a block diagram showing an electric configuration of the endoscope system including the flexible tube insertion apparatus in the first embodiment.

FIG. 1 is a block diagram showing a configuration of an endoscope system including a flexible tube insertion apparatus according to a first embodiment of the present invention. FIG. 2 is a block diagram showing an electric configuration of the endoscope system including the flexible tube insertion apparatus in the first embodiment.

Note that, as an endoscope system 1 in the embodiment explained below, an endoscope system including a so-called large intestine endoscope inserted into an intestinal canal of a subject is assumed.

As shown in FIG. 1, the endoscope system 1 according to the present embodiment includes, for example, an endoscope 10, a light source apparatus 20, a main body apparatus 30, an insertion shape detection apparatus 40, an input apparatus 50, and a display apparatus 60.

The endoscope 10 includes an insertion section 11 inserted into a subject, an operation section 12 provided on a proximal end side of the insertion section 11, and a universal cord 13 extended from the operation section 12. The endoscope 10 is configured to be removably connected to the light source apparatus 20 via a scope connector 13A provided at an end portion of the universal cord 13.

Further, the endoscope 10 is configured to be removably connected to the main body apparatus 30 via an electric connector 14A provided at an end portion of an electric cable 14 extended from the scope connector 13A. Light guides (not shown) for transmitting illumination light supplied from the light source apparatus 20 are provided inside the insertion section 11, the operation section 12, and the universal cord 13.

The insertion section 11 has flexibility and an elongated shape. The insertion section 11 is configured by providing, in order from a distal end side, a rigid distal end portion 11A, a bending portion 11B formed to be bendable, and a long flexible tube portion 11C having flexibility.

Inside the distal end portion 11A, the bending portion 11B, and the flexible tube portion 11C, a source coil group 113 (see FIG. 2, FIG. 3, and the like) in which a plurality of source coils that generate magnetic fields according to a coil driving signal supplied from the main body apparatus 30 are disposed at a predetermined interval in a longitudinal direction of the insertion section 11 is provided.

At the distal end portion 11A, an illumination window (not shown) for emitting, to an object, illumination light transmitted by the light guide provided inside the insertion section 11 is provided. At the distal end portion 11A, an image pickup unit 111 (see FIG. 2) configured to perform an operation corresponding to an image pickup control signal supplied from the main body apparatus 30 and pick up an image of the object illuminated by the illumination light emitted through an illumination window and output an image pickup signal is provided. The image pickup unit 111 includes an image sensor such as a CMOS image sensor or a CCD image sensor.

The bending portion 11B is configured to be able to bend according to operation of an angle knob 121 provided in the operation section 12.

As explained in detail below, inside a rigidity variable range equivalent to a predetermined range from a proximal end portion of the bending portion 11B to a distal end portion of the flexible tube portion 11C, a rigidity variable unit 112 configured to be able to change bending rigidity in the rigidity variable range according to control of the main body apparatus 30 is provided in the longitudinal direction of the insertion section 11. A specific configuration and the like of the rigidity variable unit 112 are explained in detail below.

Note that, in the following explanation, for convenience of explanation, "bending rigidity" is simply abbreviated as "rigidity" as appropriate. In the present embodiment, the rigidity variable range only has to be provided in at least a part of a range of the insertion section 11.

The operation section 12 has a shape that a user can grip and operate. In the operation section 12, the angle knob 121 configured to be able to perform operation for bending the bending portion 11B in upward, downward, left, and right (UDLR) four directions crossing a longitudinal axis of the insertion section 11 is provided. In the operation section 12, one or more scope switches 122 capable of performing an instruction corresponding to input operation of the user is provided.

The light source apparatus 20 includes, for example, one or more LEDs or one or more lamps as light sources. The light source apparatus 20 is configured to be able to generate illumination light for illuminating an inside of a subject into which the insertion section 11 is inserted and supply the illumination light to the endoscope 10. The light source apparatus 20 is configured to be able to change alight amount of the illumination light according to a system control signal supplied from the main body apparatus 30.

The main body apparatus 30 is configured to be removably connected to the insertion shape detection apparatus 40 via a cable 15. The main body apparatus 30 is configured to be removably connected to the input apparatus 50 via a cable 16. Further, the main body apparatus 30 is configured to be removably connected to the display apparatus 60 via a cable 17.

The main body apparatus 30 is configured to perform an operation corresponding to an instruction from the input apparatus 50 and the scope switch 122. The main body apparatus 30 is configured to perform an operation for generating an endoscopic image based on an image pickup signal outputted from the endoscope 10 and causing the display apparatus 60 to display the generated endoscopic image. Further, the main body apparatus 30 is configured to generate and output various control signals for controlling operations of the endoscope 10 and the light source apparatus 20.

In the present embodiment, the main body apparatus 30 is configured to control a driving state of the rigidity variable unit 112 based on insertion shape information (explained below) and the like outputted from the insertion shape detection apparatus 40 (see FIG. 2). Note that driving control for the rigidity variable unit 112 is explained in detail below.

The insertion shape detection apparatus 40 is configured to detect a magnetic field emitted from the source coil group 113 provided in the insertion section 11 and acquire, based on intensity of the detected magnetic field, a position of each of the plurality of source coils included in the source coil group 113.

The insertion shape detection apparatus 40 is configured to calculate an insertion shape of the insertion section 11 based on the position of each of the plurality of source coils acquired as explained above and generate insertion shape information indicating the calculated insertion shape and output the insertion shape information to the main body apparatus 30.

The input apparatus 50 includes one or more input interfaces operated by the user such as a mouse, a keyboard, or a touch panel. The input apparatus 50 is configured to be able to output an instruction corresponding to operation by the user to the main body apparatus 30.

The display apparatus 60 includes, for example, a liquid crystal monitor. The display apparatus 60 is configured to be able to display, on a screen, an endoscopic image or the like outputted from the main body apparatus 30.

<Internal Configuration of the Main Body Apparatus 30>

Subsequently, an internal configuration of the main body apparatus 30 in the present embodiment is explained with reference to FIG. 2.

FIG. 2 is a block diagram showing an electric configuration of the endoscope system including the flexible tube insertion apparatus in the first embodiment.

In the present embodiment, as shown in FIG. 2, the main body apparatus 30 includes an image processing unit 301, a rigidity control unit 302, and a control unit 303 and includes a binding-condition control unit 305 and a bending-direction detecting unit 306.

The image processing unit 301 is configured to apply, according to a system control signal outputted from the control unit 303, predetermined processing to an image pickup signal outputted from the endoscope 10 to thereby generate an endoscopic image and output the generated endoscopic image to the display apparatus 60.

The rigidity control unit 302 is configured to perform, under control by the control unit 303, an operation for controlling a driving state of the rigidity variable unit 112 based on insertion shape information outputted from an insertion-shape-information acquiring unit 402 in the insertion shape detection apparatus 40.

Note that, as explained in detail below, in the present embodiment, first, rigidity variable control is performed on the rigidity variable unit 112 by the rigidity control unit 302 explained above. On the other hand, bending rigidity of a bound section 112a configuring a part of the rigidity variable unit 112 is controlled by a binding unit 115 controlled by the binding-condition control unit 305. Therefore, "apparent bending rigidity" relating to the rigidity variable unit 112 including the binding unit 115 is controlled by the binding unit 115. Note that the "apparent bending rigidity" is explained in detail below.

Referring back to FIG. 2, the control unit 303 is configured to generate and output an image pickup control signal for controlling an image pickup operation of the image pickup unit 111. The control unit 303 is configured to generate and output a coil driving signal for driving the respective source coils included in the source coil group 113.

The control unit 303 is configured to generate a system control signal for causing the respective parts to perform an operation corresponding to an instruction from the input apparatus 50 and the scope switch 122 and outputs the generated system control signal to at least one of the light source apparatus 20 or the image processing unit 301.

Further, the control unit 303 is configured to control operations of the rigidity control unit 302, the binding-condition control unit 305, and the bending-direction detecting unit 306.

Under the control by the control unit 303, the bending-direction detecting unit 306 receives information (the insertion shape information indicating the calculated insertion shape of the insertion section 11) from the insertion-shape-information acquiring unit 402 in the insertion shape detection apparatus 40, calculates a bending direction of the insertion section 11 (for example, the flexible tube portion 11C), and sends information concerning the bending direction to the binding-condition control unit 305.

The binding-condition control unit 305 is characterized by controlling, under the control by the control unit 303, according to the information concerning the bending direction of the insertion section 11 detected by the bending-direction detecting unit 306, a binding condition relating to the binding unit 115 that binds the bound section 112a configuring a part of the rigidity variable unit 112.

The bound section 112a configuring a part of the rigidity variable unit 112 and details of the binding condition relating to the binding unit 115 are explained below.

Note that, in the present embodiment, the respective units of the main body apparatus 30 may be configured as individual electronic circuits or may be configured as circuit blocks in an integrated circuit such as an FPGA (field programmable gate array). In the present embodiment, for example, the main body apparatus 30 may include one or more processors (CPUs or the like) configured from at least one piece of hardware.

The insertion shape detection apparatus 40 includes, as shown in FIG. 2, a reception antenna 401 and an insertion-shape-information acquiring unit 402.

The reception antenna 401 includes a plurality of coils for three-dimensionally detecting a magnetic field emitted from each of the plurality of source coils included in the source coil group 113. The reception antenna 401 is configured to detect the magnetic field emitted from each of the plurality of source coils included in the source coil group 113 and generate a magnetic field detection signal corresponding to intensity of the detected magnetic field and output the magnetic field detection signal to the insertion-shape-information acquiring unit 402.

The insertion-shape-information acquiring unit 402 is configured to acquire, based on the magnetic field detection signal outputted from the reception antenna 401, a position of each of the plurality of source coils included in the source coil group 113.

The insertion-shape-information acquiring unit 402 is configured to calculate an insertion shape of the insertion section 11 based on the position of each of the plurality of source coils acquired as explained above and generate insertion shape information indicating the calculated insertion shape and output the insertion shape information to the rigidity control unit 302 and the bending-direction detecting unit 306.

More specifically, the insertion-shape-information acquiring unit 402 acquires, as the position of each of the plurality of source coils included in the source coil group 113, for example, a plurality of three-dimensional coordinate values in a space coordinate system virtually set such that a predetermined position (an anus or the like) of a subject into which the insertion section 11 is inserted is an origin or a reference point.

As processing for calculating an insertion shape of the insertion section 11, the insertion-shape-information acquiring unit 402 performs, for example, interpolation processing for interpolating the plurality of three-dimensional coordinate values acquired as explained above.

Note that, in the present embodiment, the respective units of the insertion shape detection apparatus 40 may also be configured as electronic circuits or may be configured as circuit blocks in an integrated circuit such as an FPGA (field programmable gate array). In the present embodiment, for example, the insertion shape detection apparatus 40 may include one or more processors (CPUs).

<Configuration of the Rigidity Variable Unit 112>

Subsequently, a configuration of the rigidity variable unit 112 is explained.

In the present embodiment, the rigidity variable unit 112 is configured as, for example, a not-shown actuator including a coil heater and a shape memory member and is provided in the longitudinal direction of the insertion section 11 in a predetermined range from the proximal end portion of the bending portion 11B and the distal end portion of the flexible tube portion 11C. Note that, in the present embodiment, the rigidity variable unit 112 is configured as a bar-like actuator, a cross section of which orthogonal to the longitudinal direction assumes the same shape.

As explained above, the rigidity variable control is performed on the rigidity variable unit 112 by the rigidity control unit 302. The bending rigidity of the bound section 112a configuring a part of the rigidity variable unit 112 is controlled by the binding unit 115 controlled by the binding-condition control unit 305. In other words, the "apparent bending rigidity" relating to the rigidity variable unit 112 including the binding unit 115 is controlled by the binding unit 115.

<Control of the Rigidity Variable Unit 112 by the Rigidity Control Unit 302>

Therefore, first, the rigidity control relating to the rigidity variable unit 112 by the rigidity control unit 302 is explained.

As explained above, the rigidity variable unit 112 is configured as the not-shown actuator including the coil heater and the shape memory member. The coil heater is formed by winding, in a cylindrical shape, a winding wire having high thermal conductivity such as a nichrome wire and is configured to generate heat according to the control by the rigidity control unit 302.

On the other hand, the shape memory member in the rigidity variable unit 112 is formed as an elongated member including a shape memory alloy such as nickel titanium and is disposed in a state in which the shape memory member is inserted through an internal space of the coil heater. The shape memory member is configured to be able to change elasticity according to heat emitted from the coil heater.

More specifically, the shape memory member is configured to be, for example, when heated to at least a temperature equal to or higher than a temperature TN higher than a normal temperature by heat emitted from the coil heater, a high elasticity state having a restoration force for returning to a linear shape equivalent to a shape stored in advance.

The shape memory member is configured to be, for example, when not heated to a temperature equal to or higher than the temperature TN because, for example, heat is not emitted from the coil heater, a low elasticity state not having a restoration force for returning to the linear shape equivalent to the shape stored in advance.

The rigidity control unit 302 includes a driving circuit, a memory, and a control circuit that are not shown. The driving circuit controls the coil heater according to control by the control circuit. Predetermined rigidity control information is stored in the memory. For example, rigidity control information including information indicating a rigidity variable range in the insertion section 11 and information indicating a threshold corresponding to a predetermined parameter calculated for control of the rigidity variable unit 112 is stored. The control circuit controls the driving circuit based on the rigidity control information read from the memory and the insertion shape information outputted from the insertion-shape-information acquiring unit 402.

In this way, the rigidity variable unit 112 in the present embodiment is configured to perform, first, with the rigidity control unit 302 in the main body apparatus 30, for example, operation for sequentially increasing bending rigidity in the rigidity variable range in the insertion section 11 in a direction from a center to both end portions of the rigidity variable range.

On the other hand, in the rigidity variable unit 112 in the present embodiment, under the control by the control unit 303, bending rigidity in the bound section 112a which is a part of the rigidity variable unit 112 is controlled by the binding unit 115 controlled by the binding-condition control unit 305. In other words, the rigidity variable unit 112 is characterized in that the "apparent bending rigidity" relating to the rigidity variable unit 112 including the binding unit 115 is controlled by the binding unit 115.

<Propulsion Force (Reaction) Generated in the Rigidity Variable Unit in the Insertion Section>

As explained above, in the rigidity variable unit 112 in the present embodiment, first, the bending rigidity, which is a mechanical characteristic, relating to the rigidity variable unit 112 is controlled by the control by the rigidity control unit 302. On the other hand, the bending rigidity (the apparent bending rigidity) of the rigidity variable unit 112 including the binding unit 115 is changed by the binding unit 115 controlled by the binding-condition control unit 305.

The bending rigidity of the rigidity variable unit 112 including the binding unit 115 is defined as the "apparent bending rigidity" in the present embodiment.

Further, as explained above, the bending rigidity (the apparent bending rigidity) relating to entirety of the binding unit 115 and the rigidity variable unit 112 (naturally including the bound section 112a) is changed, whereby the propulsion (the reaction) of the insertion section in which the rigidity variable unit 112 is disposed is variably controlled.

Prior to explanation of control of the "apparent bending rigidity" relating to the rigidity variable unit 112 by the binding unit 115 in the present embodiment, a relation between a bending direction of the insertion section and a propulsion force (reaction) generated in the rigidity variable unit is explained with reference to FIG. 9 to FIG. 12.

Figure 9:
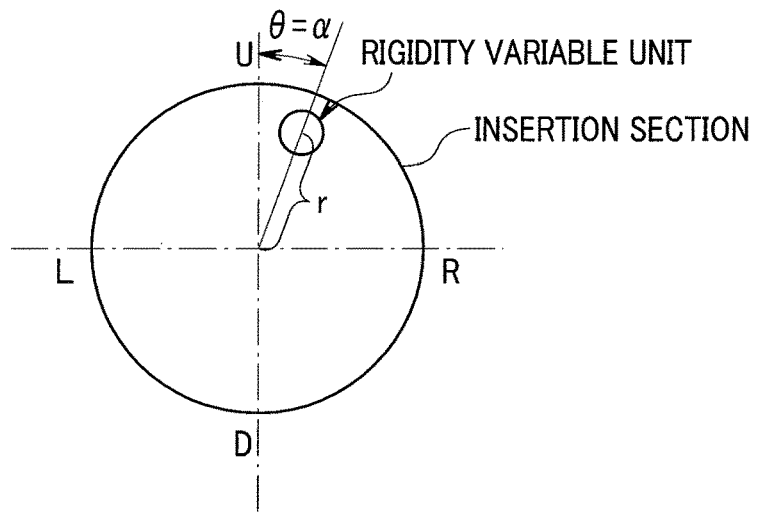
FIG. 9 is a diagram for explaining a propulsion force (reaction) generated in the rigidity variable unit in the insertion section and is a diagram showing a positional relation of the rigidity variable unit in the insertion section.
Figure 10:
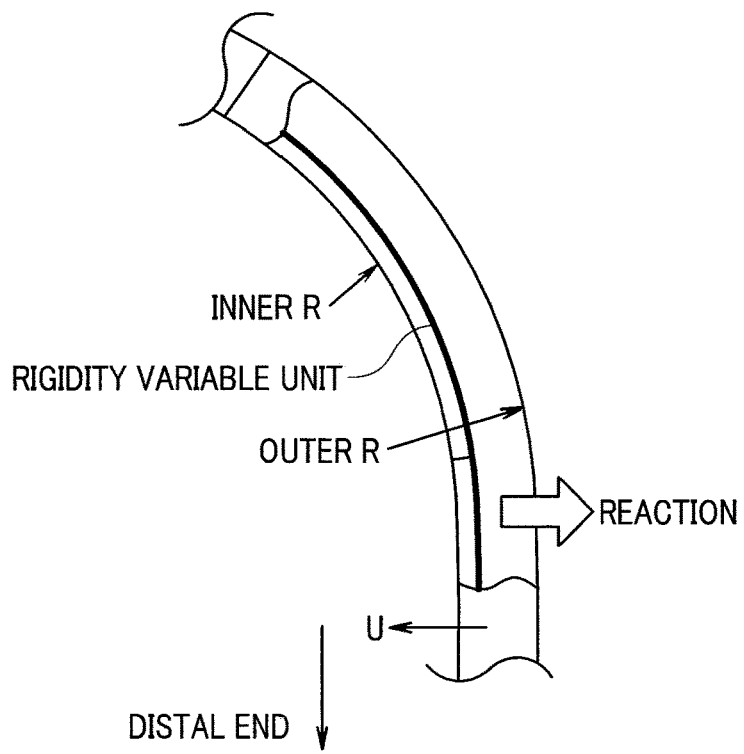
FIG. 10 is a diagram for explaining a propulsion force (reaction) generated in the rigidity variable unit in the insertion section.

FIG. 9 is a diagram for explaining a propulsion force (reaction) generated in the rigidity variable unit in the insertion section and is a diagram showing a positional relation of the rigidity variable unit in the insertion section.

In general, the rigidity variable unit disposed in the insertion section is disposed in an "offset position" separated by an approximate radius r from a center axis in a predetermined bending direction, for example, a substantial U direction (a direction separated at a slight angle $\theta=\alpha$ from the U direction) shown in FIG. 9 in a cross section orthogonal to the longitudinal direction of the insertion section.

It is assumed that the rigidity variable unit is firmly fixed (completely bound) to the insertion section in the "offset position". When the flexible tube portion of the insertion section is bent in the U direction under a condition that the rigidity variable unit is firmly fixed (completely bound) to the insertion section in this way, the rigidity variable unit is disposed in a position on an inner side of an inside of the insertion section (a position of inner R in FIG. 10). On the other hand, when the flexible tube portion of the insertion section is bent in an opposite downward direction (D direction), the rigidity variable unit is disposed in a position on an outer side of the inside of the insertion section (a position of outer R in FIG. 10).

Figure 11:
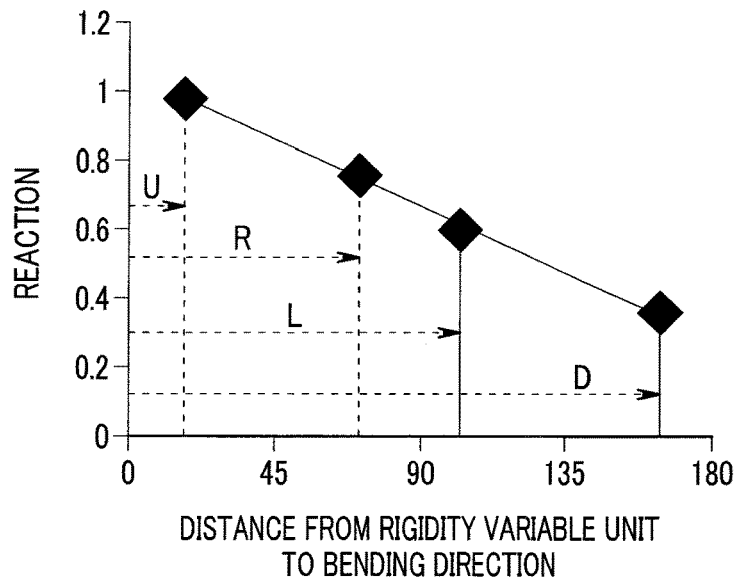
FIG. 11 is a diagram for explaining a propulsion force (reaction) generated in the rigidity variable unit in the insertion section and is a diagram showing a relation between a position of the rigidity variable unit in the insertion section and the reaction.

When respective bending reactions (=propulsion forces) in the inner R (the bending in the U direction) and the outer R (the bending in the D direction) are compared, it is seen that the bending in the U direction is larger (see FIG. 11). In other words, it is seen that, when the rigidity variable unit disposed in the insertion section is disposed to be offset in the predetermined bending direction in the cross section orthogonal to the longitudinal direction of the insertion section (as explained above, this is common in the endoscope insertion section of the related art), reaction (=a propulsion force) generated for the insertion section (the rigidity variable unit) fluctuates depending on a bending direction of the insertion section.

Figure 12:
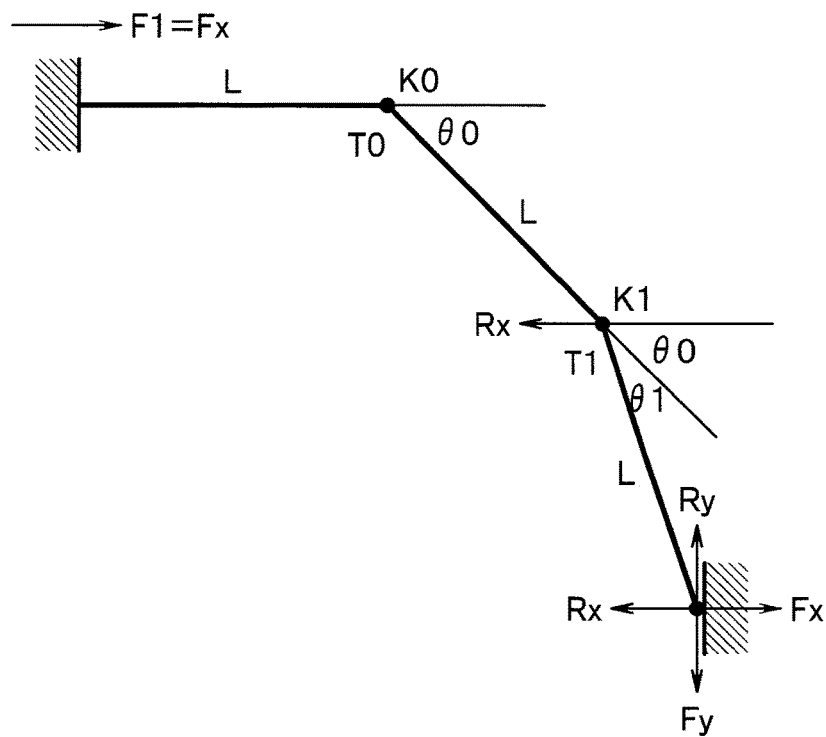
FIG. 12 is a diagram showing a model for explaining a propulsion force (reaction) generated in the rigidity variable unit in the insertion section.

On the other hand, a reason why the propulsion force of the insertion section (the rigidity variable unit) can be increased when hardness of the insertion section distal end portion is increased is explained with reference to a model shown in FIG. 12.

In the model shown in FIG. 12, when
$T_0$, $T_1$: torques of a rotating unit
$K_0$, $K_1$: rotation spring rigidities ($K_0=K_1$)
$\theta_0$, $\theta_1$: rotation angles
L: link length
$F_x$: a force applied to a wall by a link
$F_y$: a propulsion force
$R_x$: reaction of $F_x$
$R_y$: reaction of $F_y$,
a balance of the torques can be represented by equations described below.

$$T_0 = K_0\theta_0 = R_x \cdot L \sin\theta_0 - R_y L \cos\theta_0 + T_1 \quad (1)$$

$$T_1 = K_1\theta_1 = R_x \cdot L \sin(\theta_0+\theta_1) - R_y L \cos(\theta_0+\theta_1) \quad (2)$$

When $R_x$ and $R_y$ are solved from Equations (1) and (2), Equations (3) and (4) below are obtained.

$$R_x = T_1 \cos\theta_0 + (T_1-T_0)\cdot\cos(\theta_0+\theta_1)/L \sin\theta_1 \quad (3)$$

$$R_y = T_1 \sin\theta_0 + (T_1-T_0)\cdot\sin(\theta_0+\theta_1)/L \sin\theta_1 \quad (4)$$

From a low of action and reaction,
$F_x = R_x = F_1$
$F_y = R_y$.
When
$T_0 = K_0\theta_0$
$T_1 = K_1\theta_1$
are substituted in Equations (3) and (4), the following Equation (5) is obtained.

$$R_y = K_1\theta_1(\sin\theta_0+\sin(\theta_0+\theta_1))-K_0\theta_0\cdot\sin(\theta_0+\theta_1)/L \sin\theta \quad (5)$$

It is seen from this that, in order to improve the propulsion $F_y$ (=$R_y$), from Equation (5), $K_1$ only has to be larger than $K_0$.

In view of these kinds of knowledge, the present invention provides means for controlling bending rigidity of the distal end portion of the insertion section 11 (in this embodiment, equivalent to a distal end portion (the bound section 112a) of the rigidity variable unit 112 disposed in a range from a proximal end portion of the bending portion 11B to a distal end portion of the flexible tube portion 11C) to appropriately control the propulsion force of the insertion section 11.

<Control of the Rigidity Variable Unit 112 by the Binding Unit 115>

The control of the "apparent bending rigidity" of the rigidity variable unit 112 by the binding unit 115 explained above in the present embodiment is explained in detail below.

Figure 3:
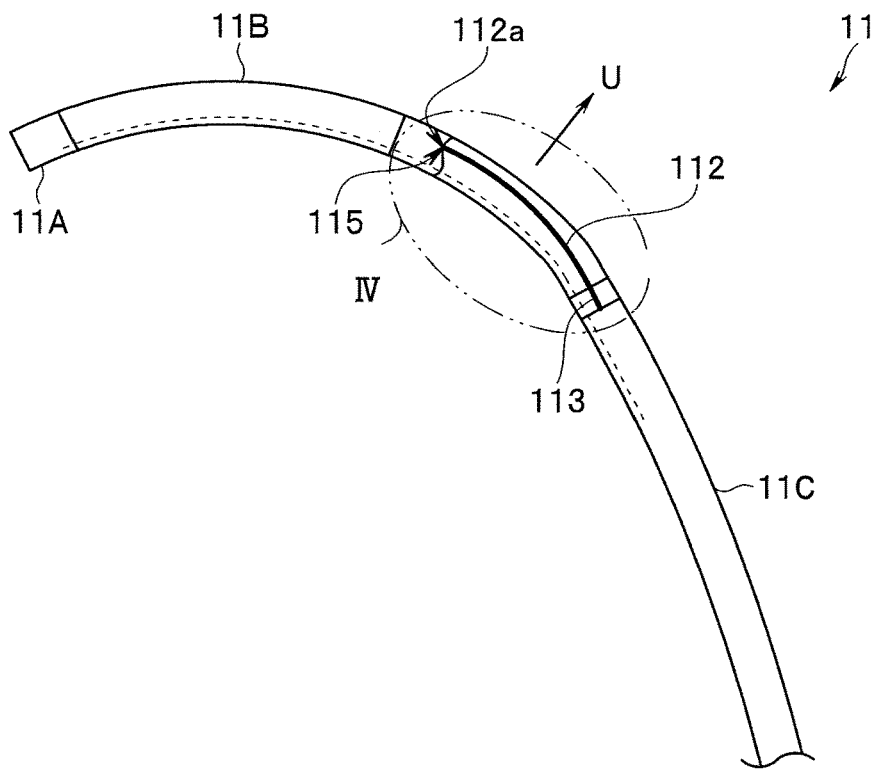
FIG. 3 is a main part enlarged view showing a vicinity of an insertion section distal end portion including the flexible tube insertion apparatus in the first embodiment.
Figure 4:
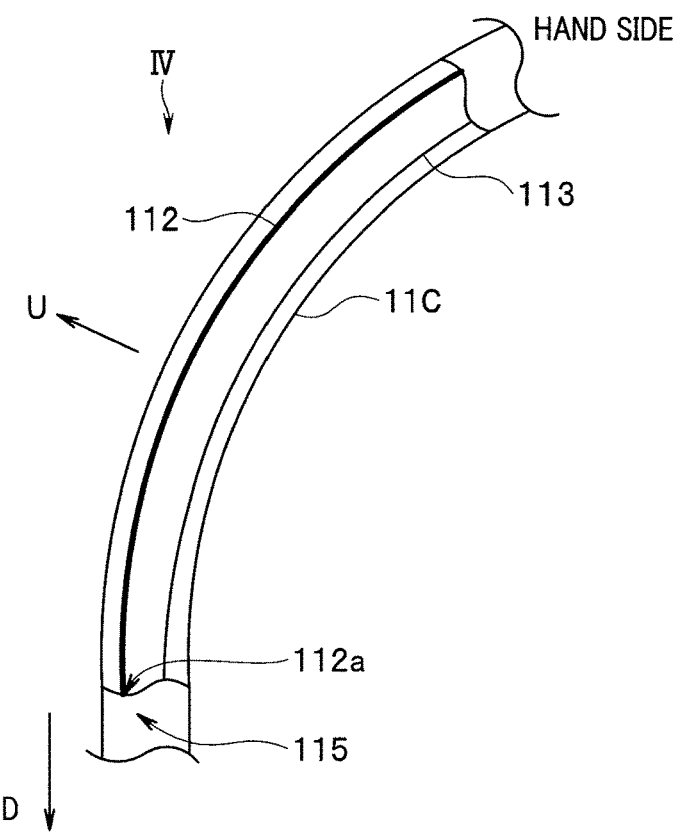
FIG. 4 is a main part enlarged view further enlarging and showing the flexible tube insertion apparatus in the first embodiment shown in FIG. 3.
Figure 5:
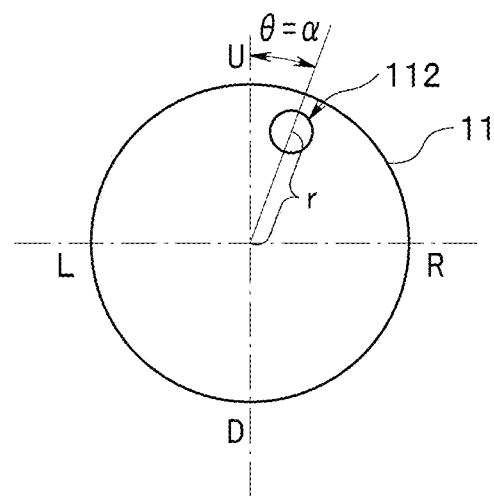
FIG. 5 is a diagram showing a positional relation of a rigidity variable unit in an insertion section in the flexible tube insertion apparatus in the first embodiment.
Figure 6A:
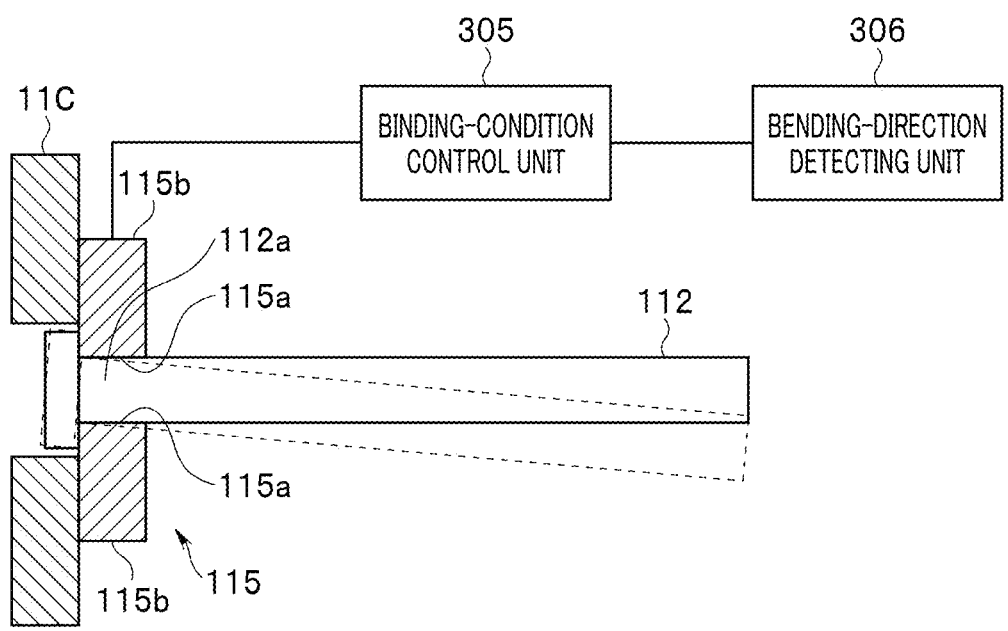
FIG. 6A is a side sectional view showing a schematic configuration of the flexible tube insertion apparatus in the first embodiment.
Figure 6B:
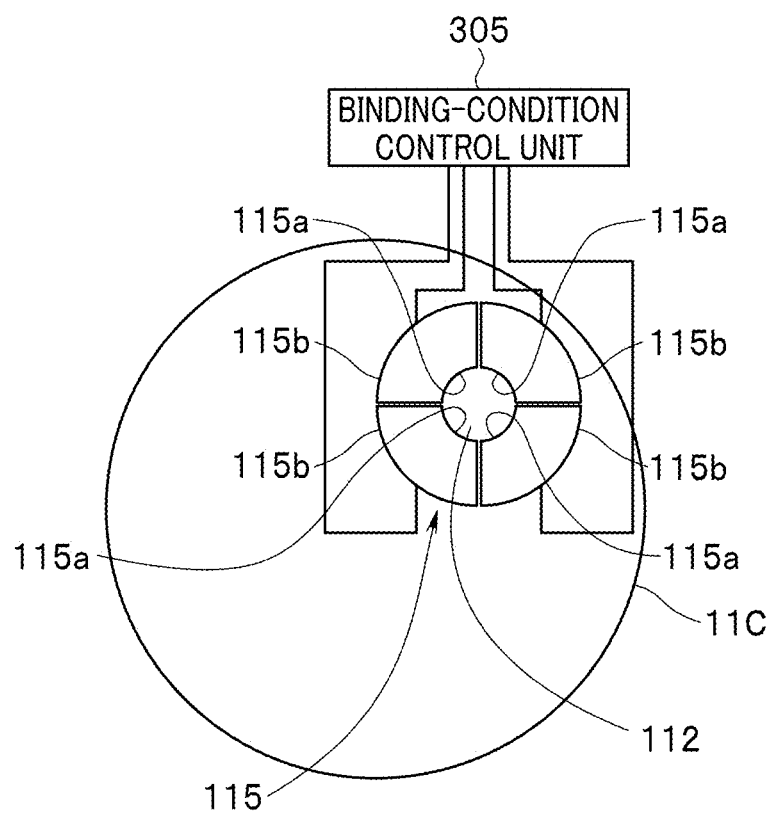
FIG. 6B is a front view showing the schematic configuration of the flexible tube insertion apparatus of FIG. 6A.

FIG. 3 is a main part enlarged view showing a vicinity of an insertion section distal end portion including the flexible tube insertion apparatus in the first embodiment. FIG. 4 is a main part enlarged view further enlarging and showing the flexible tube insertion apparatus in the first embodiment shown in FIG. 3. FIG. 5 is a diagram showing a positional relation of a rigidity variable unit in the insertion section in the flexible tube insertion apparatus in the first embodiment. FIG. 6A is a side sectional view showing a schematic configuration of the flexible tube insertion apparatus in the first embodiment. FIG. 6B is a front view showing the schematic configuration of the flexible tube insertion apparatus of FIG. 6A.

Note that FIG. 3 shows the rigidity variable unit 112 disposed on an inside by removing an outer skin portion on the distal end side of the flexible tube portion 11C in the insertion section 11. FIG. 4 is a diagram enlarging and showing the distal end side in the flexible tube portion 11C shown in FIG. 3.

In the present embodiment, the rigidity variable unit 112 is configured as the not-shown actuator including the coil heater and the shape memory member as explained above. As shown in FIG. 3 and FIG. 4, the rigidity variable unit 112 is provided in the longitudinal direction of the insertion section 11 in the predetermined range from the proximal end portion of the bending portion 11B to the distal end portion of the flexible tube portion 11C. Note that, as shown in FIG. 3 and FIG. 4, the source coil group 113 is provided in the longitudinal direction of the insertion section 11 inside the distal end portion 11A, the bending portion 11B, and the flexible tube portion 11C As shown in FIG. 5, the rigidity variable unit 112 is disposed in the "offset position" separated by the approximate radius r from the center axis in the substantial U direction (the direction separated at the slight angle θ=α from the U direction) in the cross section orthogonal to the longitudinal direction of the insertion section 11.

As explained above, the variable control for the rigidity of the rigidity variable unit 112 is performed by the rigidity control unit 302 and, under the control by the control unit 303, the "apparent bending rigidity" of the rigidity variable unit 112 is controlled by the binding unit 115 controlled by the binding-condition control unit 305

The binding unit 115 and the "bound section 112a" in the rigidity variable unit 112, the bending rigidity of which is controlled by the binding unit 115, are explained below.

Figure 7:
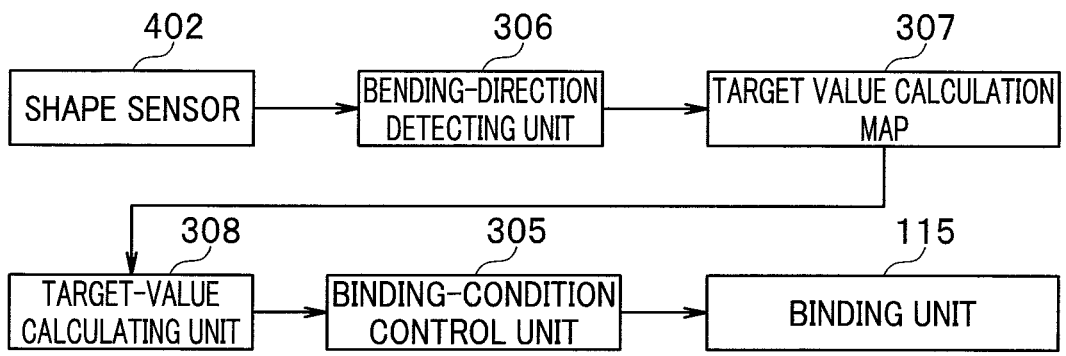
FIG. 7 is a diagram for explaining a control method for a binding unit in the flexible tube insertion apparatus in the first embodiment.
Figure 8:
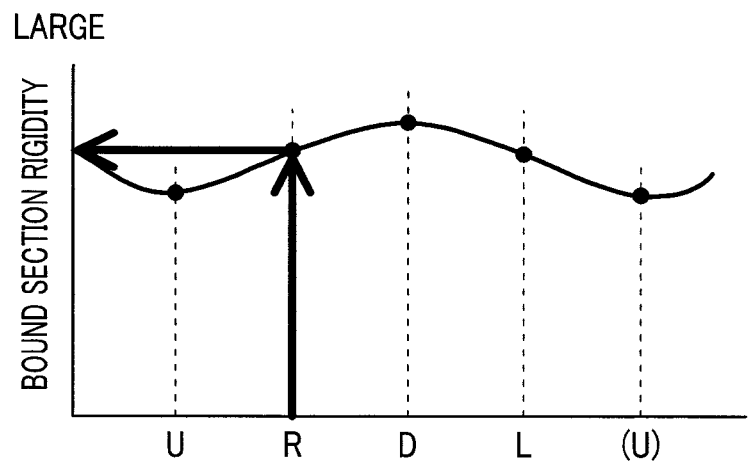
FIG. 8 is a diagram showing an example of a target value calculation map for setting a target value of bending rigidity relating to a bound section in the flexible tube insertion apparatus in the first embodiment.

FIG. 6A is a side sectional view showing a schematic configuration of the flexible tube insertion apparatus in the first embodiment. FIG. 6B is a front view showing the schematic configuration of the flexible tube insertion apparatus of FIG. 6A. FIG. 7 is a diagram for explaining a control method for the binding unit in the flexible tube insertion apparatus in the first embodiment. FIG. 8 is a diagram showing an example of a target value calculation map for setting a target value of bending rigidity relating to a bound section in the flexible tube insertion apparatus in the first embodiment.

In the present embodiment, the rigidity variable unit 112 is configured as a bar-like actuator, a cross section of which orthogonal to the longitudinal direction assumes the same shape. As shown in FIG. 6A, the bound section 112a, which is a most distal end portion of the rigidity variable unit 112, engages with the binding unit 115, or the plurality of plate-like members 115b as shown in FIG. 6B, in a boundary portion between the distal end portion of the flexible tube portion 11C and the proximal end portion of the bending portion 11B in the insertion section 11.

The binding unit 115 is configured by a plurality of plate-like members formed by a shape memory alloy. All of these plurality of binding units 115 are disposed in positions facing an outer circumferential surface of the bound section 112a, which is an end point of the rigidity variable unit 112.

As shown in FIG. 6B, the plurality of plate-like members 115b are disposed, for example, in four directions at 90 degree intervals in a circumferential direction of an outer circumferential surface of the bound section 112a facing the plurality of plate-like members 115b such that the plurality of plate-like members 115b are in a state in which extending and contracting directions of the respective plurality of plate-like members 115b are in a normal direction of the outer circumference and the plurality of plate-like members 115b are disposed at equal intervals in the circumferential direction.

Further, FIGS. and 6B show a plurality of plate-like members 115b disposed circumferentially around an outer circumferential surface of the bound section 112a. That is, end faces 115a in the extending and contracting directions of all of the plurality of plate-like members 115b are in contact with the outer circumferential surface of the bound section 112a that faces the plurality of plate-like members 115b.

In other words, the bound section 112a, which is the end point of the rigidity variable unit 112, is bound by being sandwiched by the plurality of binding units 115 (for example, four binding units 115).

All of the plurality of binding units 115 are connected to the binding-condition control unit 305. A voltage corresponding to a binding condition calculated by the binding-condition control unit 305 is applied to the plurality of binding units 115. In other words, extension and contraction of the plurality of binding units 115 is controlled according to the voltage applied from the binding-condition control unit 305.

A pressing force (a binding force) received from the one end face 115a in contact with the outer circumferential surface of the bound section 112a also changes according to the extension and contraction of the plurality of binding units 115 controlled by the binding-condition control unit 305.

The "pressing force" generated on the outer circumferential surface of the bound section 112a changes, whereby bending rigidity in the bound section 112a also changes. The bending rigidity of the bound section 112a, which is the end point of the rigidity variable unit 112 extended in the longitudinal direction, changes, whereby, as a result, rigidity of the rigidity variable unit 112 itself also changes.

<Action in the First Embodiment>

Subsequently, in the present embodiment, rigidity control for the rigidity variable unit 112 by the binding unit 115 controlled by the binding-condition control unit 305 is explained with reference to FIG. 7 and FIG. 8.

As shown in FIG. 7, in the present embodiment, first, the insertion-shape-information acquiring unit 402 (in FIG. 7, described as a shape sensor 402) in the insertion shape detection apparatus 40 detects a magnetic field emitted from the source coil group 113 provided in the insertion section 11 and calculates an insertion shape of the insertion section 11 based on intensity of the detected magnetic field and a position of each of the plurality of source coils included in the source coil group 113.

The insertion-shape-information acquiring unit 402 generates insertion shape information indicating the calculated insertion shape and outputs the insertion shape information to the main body apparatus 30. In the main body apparatus 30, under the control by the control unit 303, the bending-direction detecting unit 306 receives information (the insertion shape information indicating the calculated insertion shape of the insertion section 11) from the insertion-shape-information acquiring unit 402 in the insertion shape detection apparatus 40 and calculates a bending direction of the insertion section 11 (for example, the flexible tube portion 11C).

At this time, the bending-direction detecting unit 306 calculates a target value of a bending rigidity value of the bound section 112a based on information concerning the bending direction of the insertion section 11 calculated by the insertion-shape-information acquiring unit 402 and information of a predetermined target value calculation map 307. Note that, at this time, the bending-direction detecting unit 306 plays a function of a target-value calculating unit 308 that calculates the target value of the bending rigidity value of the bound section 112a.

For example, if the insertion section 11 bends in a right direction (R direction), the target-value calculating unit 308 in the bending-direction detecting unit 306 calculates a rigidity target value based on the target value calculation map shown in FIG. 8 and sends a result of the calculation to the binding-condition control unit 305.

Thereafter, the binding-condition control unit 305 calculates a "binding condition" based on the rigidity target value and controls the binding unit 115. More specifically, the binding-condition control unit 305 calculates, based on the rigidity target value, a voltage applied to the binding unit 115 configured by the shape memory alloy and applies the voltage to the binding unit 115.

The binding unit 115 is displaced to a predetermined shape by the voltage applied from the binding-condition control unit 305. On the other hand, a "pressing force" corresponding to the target value is applied to the bound section 112a by the shape displacement of the binding unit 115. Consequently, a binding force of the bound section 112a by the binding unit 115 also increases.

The bending rigidity of the bound section 112a, which is the end point of the rigidity variable unit 112, increases in this way, whereby the "apparent bending rigidity" of the rigidity variable unit 112 itself also increases.

The bending rigidity of the rigidity variable unit 112 increases, whereby rigidity near the distal end portion of the insertion section 11 (a range from the proximal end portion of the bending portion 11B to the distal end portion of the flexible tube portion 11C) also increases. By properly setting the target value calculation map, in the case of the large intestine endoscope in the present embodiment, it is possible to suppress fluctuation in a force applied to an intestinal wall of a large intestine and a propulsion force of the insertion section distal end portion.

In other words, according to the present embodiment, irrespective of a bending direction of the insertion section 11, it is possible to make a load to the intestinal wall of the large intestine uniform and keep the propulsion force of the insertion section 11 constant. Consequently, it is possible to improve insertability of the insertion section 11 while reducing a burden on a subject.

Note that, in the present embodiment, a magnetic sensor type is adopted as the insertion shape detection apparatus 40. However, not only this, but the insertion shape detection apparatus may adopt a shape sensor and an insertion amount sensor or may be, for example, a type using a ultras sound type, optical type, or acceleration sensor. In other words, the insertion shape detection apparatus only has to be able to detect a position or a relative position of the insertion section 11 with respect to a subject or with respect to a place such as an inside of a room where the subject is placed.

More specifically, for example, the insertion amount sensor may be a sensor including a rotation amount (torsion amount) sensor according to necessity. By detecting a rotation amount (a torsion amount) of the insertion section inserted into a subject (a patient), it is possible to more accurately calculate a relative position with respect to the subject (the patient).

Second Embodiment

A second embodiment of the present invention is explained.

A flexible tube insertion apparatus in the second embodiment is characterized by appropriately setting a target value relating to bending rigidity of the bound section 112a according to a disposition position in the insertion section of the rigidity variable unit 112, more specifically, according to a separation distance from a center axis of the insertion section 11.

Since the other components are the same as the components in the first embodiment, only differences from the first embodiment are explained. Explanation about common portions is omitted.

Figure 13:
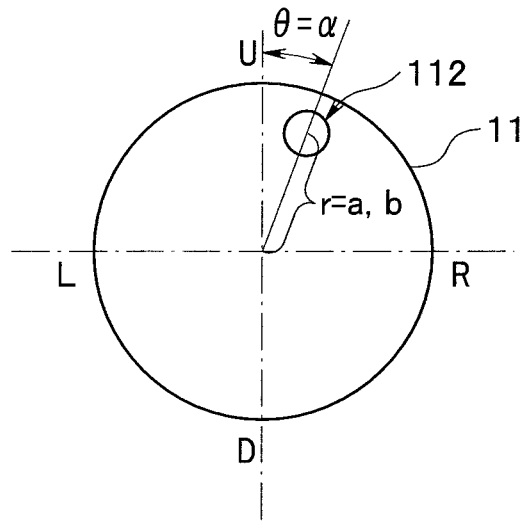
FIG. 13 is a diagram showing a positional relation of a rigidity variable unit in an insertion section in a flexible tube insertion apparatus in a second embodiment of the present invention.
Figure 14:
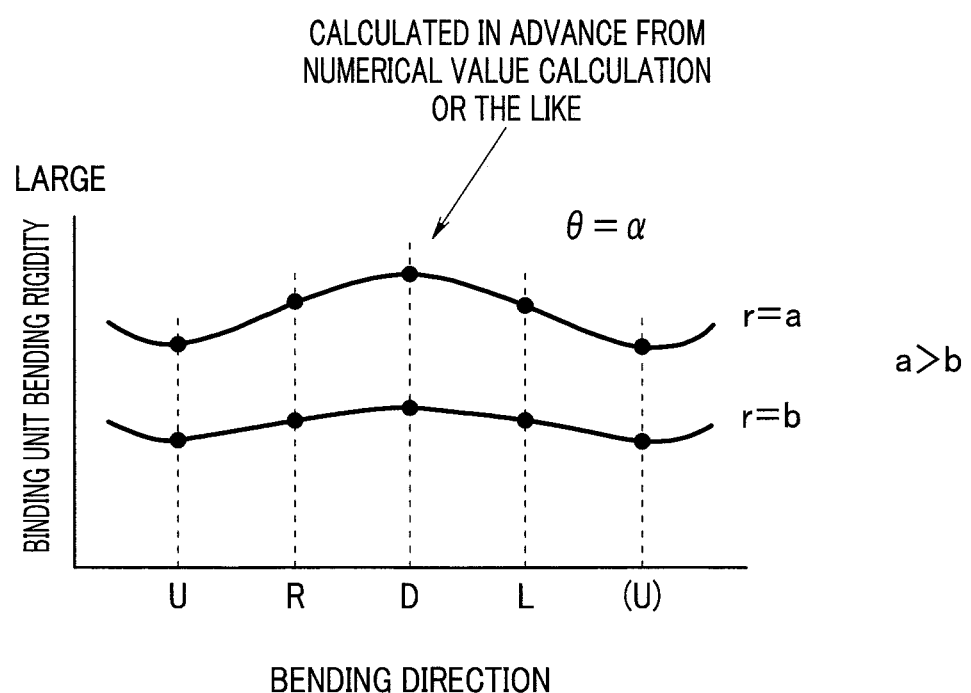
FIG. 14 is a diagram showing an example of a target value calculation map for setting a target value of bending rigidity relating to a bound section in the flexible tube insertion apparatus in the second embodiment.

FIG. 13 is a diagram showing a positional relation of a rigidity variable unit in an insertion section in the flexible tube insertion apparatus in the second embodiment of the present invention. FIG. 14 is a diagram showing an example of a target value calculation map for setting a target value of bending rigidity relating to a bound section in the flexible tube insertion apparatus in the second embodiment.

In the first embodiment explained above, only a case is considered in which the rigidity variable unit 112 is disposed in the "offset position" separated by the approximate "predetermined radius r" from the center axis in the substantial U direction (the direction separated at the slight angle θ=α from the U direction) in the cross section orthogonal to the longitudinal direction of the insertion section 11.

However, when the "predetermined radius r" is displaced, reaction (=a propulsion force) applied to the insertion section involved in bending of the insertion section is also displaced. Therefore, it is desirable to change the target value of the bending rigidity relating to the bound section 112a as well.

In view of such circumstances, the second embodiment is characterized in that the target value calculation map of bending rigidity relating to the bound section 112a is set according to the displacement at the "predetermined radius r".

More specifically, in the second embodiment, as shown in FIG. 13 and FIG. 14, the rigidity variable unit 112 sets the target value calculation map of bending rigidity respectively corresponding to positions separated by an approximate radius r=a or b (a>b) from the center axis of the insertion section 11.

In this way, with the flexible tube insertion apparatus in the second embodiment, it is possible to appropriately set a target value of bending rigidity of the bound section 112a of the rigidity variable unit 112 according to a disposition position of the rigidity variable unit 112 (a separation distance from the center axis of the insertion section) in the insertion section 11.

Third Embodiment

A third embodiment of the present invention is explained.

A flexible tube insertion apparatus in the third embodiment is characterized by appropriately setting a target value relating to bending rigidity of the bound section 112a according to a disposition position of the rigidity variable unit 112 in the insertion section, more specifically, according to in which bending direction of the insertion section 11 the rigidity variable unit 112 is disposed.

Since the other components are the same as the components in the first embodiment, only differences from the first embodiment are explained. Explanation about common portions is omitted.

Figure 15:
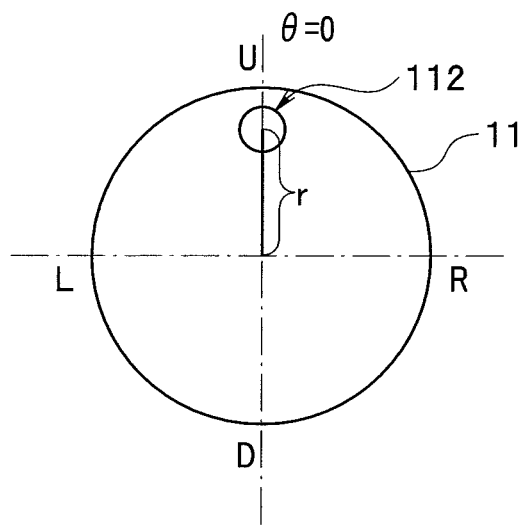
FIG. 15 is a diagram showing a positional relation (θ=0) of a rigidity variable unit in an insertion section in a flexible tube insertion apparatus in a third embodiment of the present invention.
Figure 16:
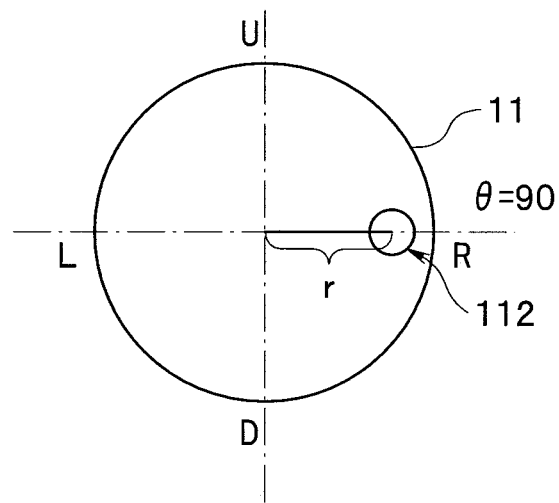
FIG. 16 is a diagram showing a positional relation (θ=90) of the rigidity variable unit in the insertion section in the flexible tube insertion apparatus in the third embodiment.
Figure 17:
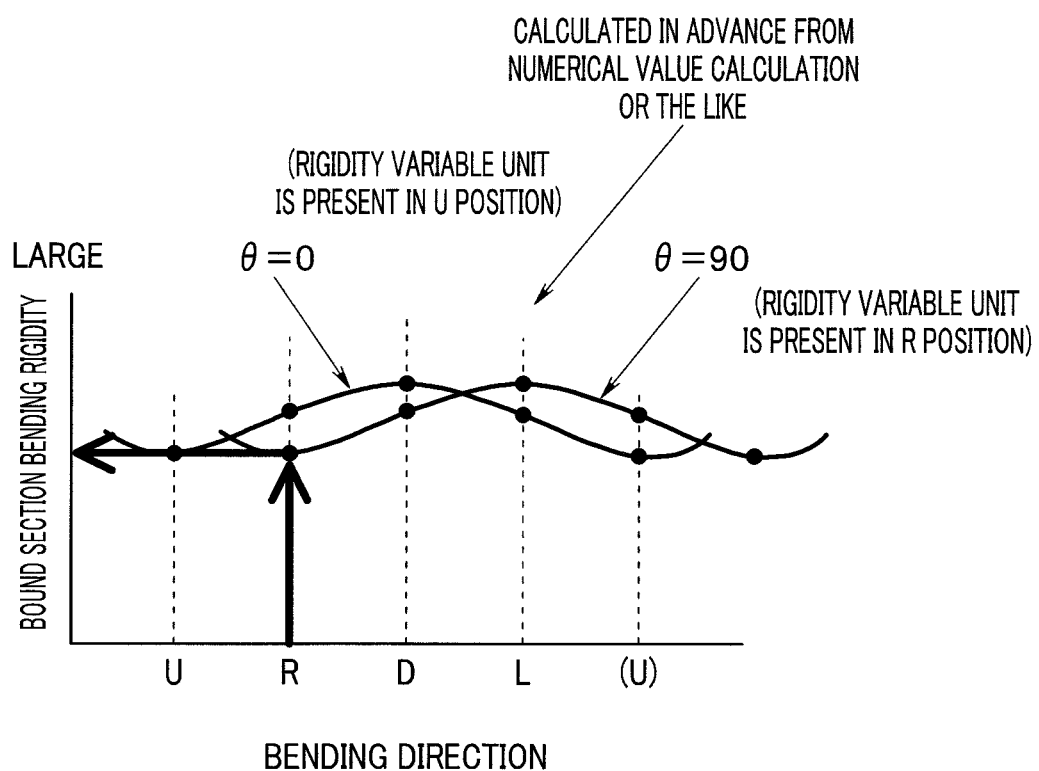
FIG. 17 is a diagram showing an example of a target value calculation map for setting a target value of bending rigidity relating to a bound section in the flexible tube insertion apparatus in the third embodiment.

FIG. 15 is a diagram showing a positional relation (θ=0) of a rigidity variable unit in an insertion section in the flexible tube insertion apparatus in the third embodiment of the present invention. FIG. 16 is a diagram showing a positional relation (θ=90) of the rigidity variable unit in the insertion section in the flexible tube insertion apparatus in the third embodiment. FIG. 17 is a diagram showing an example of a target value calculation map for setting a target value of bending rigidity relating to a bound section in the flexible tube insertion apparatus in the third embodiment.

In the first embodiment explained above, only a case is considered in which the rigidity variable unit 112 is disposed in the "offset position" separated by the approximate "predetermined radius r" from the center axis in the substantial U direction (the direction separated at the slight angle θ=α from the U direction) in the cross section orthogonal to the longitudinal direction of the insertion section 11.

However, since reaction (=a propulsion force) applied to the insertion section involved in bending of the insertion section is also displaced according to in which "bending direction" of the insertion section 11 the rigidity variable unit 112 is disposed, it is desirable to change a target value of bending rigidity relating to the bound section 112a according to the "bending direction" in which the rigidity variable unit 112 is disposed.

In view of such circumstances, the third embodiment is characterized in that the target value calculation map of bending rigidity relating to the bound section 112a is set according to the "bending direction" in which the rigidity variable unit 112 are disposed.

More specifically, in the third embodiment, as shown in FIG. 15, FIG. 16, and FIG. 17, the target value calculation map of bending rigidity respectively corresponding to a case in which the rigidity variable unit 112 is disposed in the U direction of the insertion section 11 and a case in which the rigidity variable unit 112 is disposed in an R direction.

In this way, with the flexible tube insertion apparatus in the third embodiment, it is possible to appropriately set a target value of bending rigidity of the bound section 112a according to a "bending direction" in which the rigidity variable unit 112 is disposed in the insertion section 11.

Fourth Embodiment

A fourth embodiment of the present invention is explained.

In the flexible tube insertion apparatus in the first embodiment explained above, the bound section, which is the end point of the rigidity variable unit, is bound by the binding unit configured by the shape memory alloy and the bending rigidity of the bound section is controlled. However, a flexible tube insertion apparatus in the fourth embodiment is different in the binding unit that binds the bound section, which is the end point of the rigidity variable unit.

Since the other components are the same as the components in the first embodiment, only differences from the first embodiment are explained. Explanation about common portions is omitted.

Figure 18:
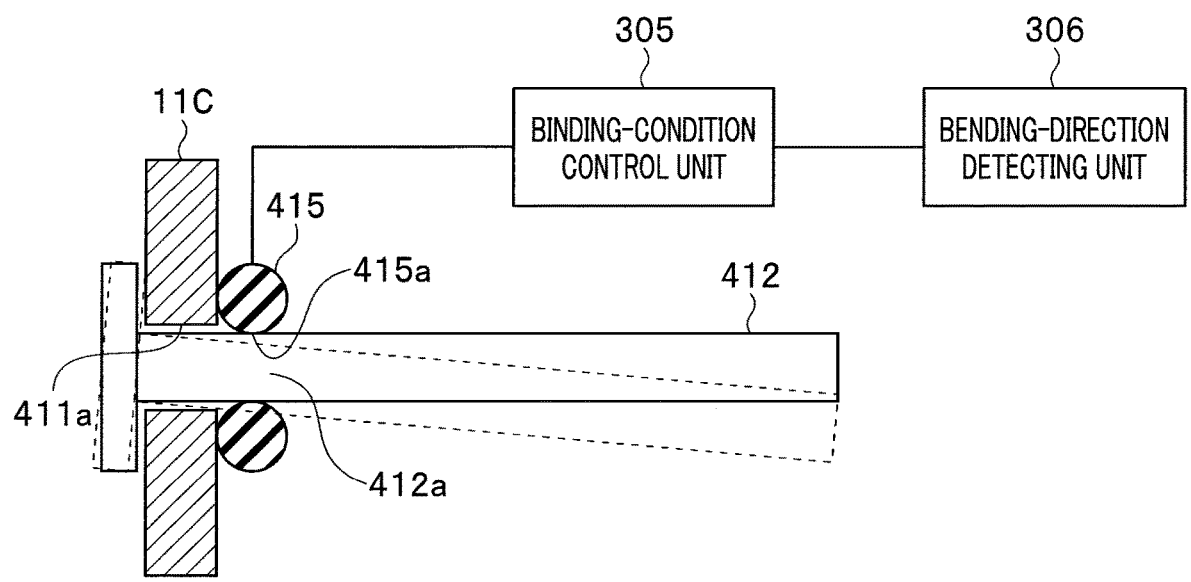
FIG. 18 is a side sectional view showing a schematic configuration of a flexible tube insertion apparatus in a fourth embodiment of the present invention.

FIG. 18 is a side sectional view showing a schematic configuration of the flexible tube insertion apparatus in the fourth embodiment of the present invention.

As shown in FIG. 18, in the fourth embodiment, like the rigidity variable unit 112 in the first embodiment, a rigidity variable unit 412 is configured as a not-shown actuator including a coil heater and a shape memory member and is provided in the longitudinal direction of the insertion section 11 in the predetermined range from the proximal end portion of the bending portion 11B and the distal end portion of the flexible tube portion 11C.

As in the first embodiment, the rigidity variable unit 412 is disposed in the "offset position" separated by the approximate radius r from the center axis in the substantial U direction (the direction separated at the slight angle θ=α from the U direction) in the cross section orthogonal to the longitudinal direction of the insertion section 11 (see FIG. 5).

Further, as in the first embodiment, variable control of rigidity of the rigidity variable unit 412 is performed by the rigidity control unit 302 and, under the control by the control unit 303, bending rigidity of the rigidity variable unit 412 is controlled by a binding unit 415 controlled by the binding-condition control unit 305.

In the fourth embodiment, the binding unit 415 is configured as a balloon assuming a ring shape that covers an outer circumferential surface of a bound section 412a, which is an end point in the rigidity variable unit 412, in a circumferential direction. An inner circumferential surface of the binding unit 415 having the ring shape is disposed in contact with the outer circumferential surface of the bound section 412a facing the inner circumferential surface.

In other words, in the fourth embodiment, the bound section 412a, which is the end point of the rigidity variable unit 412, is bound by the inner circumferential surface of the binding unit 415 having the ring shape.

A size of the binding unit 415 is displaced, that is, an internal volume of the binding unit 415 is displaced according to magnitude of an air pressure applied to an inside of the binding unit 415. For example, if the air pressure applied to the inside is large, the internal volume increases and an external shape is expanded. On the other hand, if the air pressure applied to the inside is small, the internal volume decreases and the external shape is reduced.

Further, the binding unit 415 is connected to the binding-condition control unit 305 as in the first embodiment. The air pressure corresponding to a binding condition calculated by the binding-condition control unit 305 is applied to the binding unit 415. In other words, the internal volume of the binding unit 415 is controlled and the expansion and reduction of the external shape of the binding unit 415 is controlled according to the air pressure applied from the binding-condition control unit 305.

A pressing force (a binding force) received by the bound section 412a from the inner circumferential surface of the binding unit 415 also changes according to the expansion or reduction of the binding unit 415 controlled by the binding-condition control unit 305.

The "pressing force" generated on the outer circumferential surface of the bound section 412a changes, whereby, as in the first embodiment, bending rigidity in the bound section 412a also changes. The bending rigidity of the bound section 412a, which is the end point of the rigidity variable unit 412 extended in the longitudinal direction, changes, whereby, as a result, rigidity of the rigidity variable unit 412 itself also changes.

Note that, in the fourth embodiment, an end portion of the rigidity variable unit 412 is held by a part of the flexible tube portion 11C in a vicinity of the bound section 412a in contact with the binding unit 415. However, since the rigidity variable unit 412 is slightly displaced according to the expansion or reduction of the binding unit 415, a slight gap 411a is formed between a holding section of the flexible tube portion 11C and the end portion of the rigidity variable unit 412 facing the holding section.

<Action in the Fourth Embodiment>

In the fourth embodiment, rigidity control for the rigidity variable unit 412 by the binding unit 415 controlled by the binding-condition control unit 305 is the same as the rigidity control in the first embodiment explained above (see, for example, FIG. 7 and FIG. 8). Therefore, detailed explanation of the rigidity control is omitted. In the fourth embodiment, the binding-condition control unit 305 calculates a "binding condition" based on the same rigidity target value as the rigidity target value in the first embodiment and controls the binding unit 415.

The binding unit 415 is displaced to a predetermined shape by an air pressure applied from the binding-condition control unit 305. On the other hand, a "pressing force" corresponding to the target value is applied to the bound section 412a by the shape displacement of the binding unit 415. Consequently, a binding force of the bound section 412a by the binding unit 415 also increases. Bending rigidity relating to the bound section 412a also increases.

In this way, in the fourth embodiment as well, the bending rigidity of the bound section 412a, which is the end point of the rigidity variable unit 412, increases, whereby "apparent bending rigidity" of the rigidity variable unit 412 itself also increases.

The "apparent bending rigidity" of the rigidity variable unit 412 increases, whereby rigidity near the distal end portion of the insertion section 11 (the range from the proximal end portion of the bending portion 11B to the distal end portion of the flexible tube portion 11C) also increases. By properly setting the target value calculation map, in the case of the large intestine endoscope in the present embodiment, it is possible to suppress fluctuation in a force applied to an intestinal wall of a large intestine and a propulsion force of the insertion section distal end portion.

In other words, according to the fourth embodiment, as in the first embodiment, irrespective of a bending direction of the insertion section 11, it is possible to make a load to the intestinal wall of the large intestine uniform and keep the propulsion force of the insertion section 11 constant. Consequently, it is possible to improve insertability of the insertion section 11 while reducing a burden on a subject.

Fifth Embodiment

A fifth embodiment of the present invention is explained.

In the flexible tube insertion apparatus in the first embodiment explained above, the bound section, which is the end point of the rigidity variable unit, is bound by the binding unit configured by the shape memory alloy and the bending rigidity of the bound section is controlled. However, a flexible tube insertion apparatus in the fifth embodiment is different in the binding unit that binds the bound section, which is the end point of the rigidity variable unit.

Since the other components are the same as the components in the first embodiment, only differences from the first embodiment are explained. Explanation about common portions is omitted.

Figure 19:
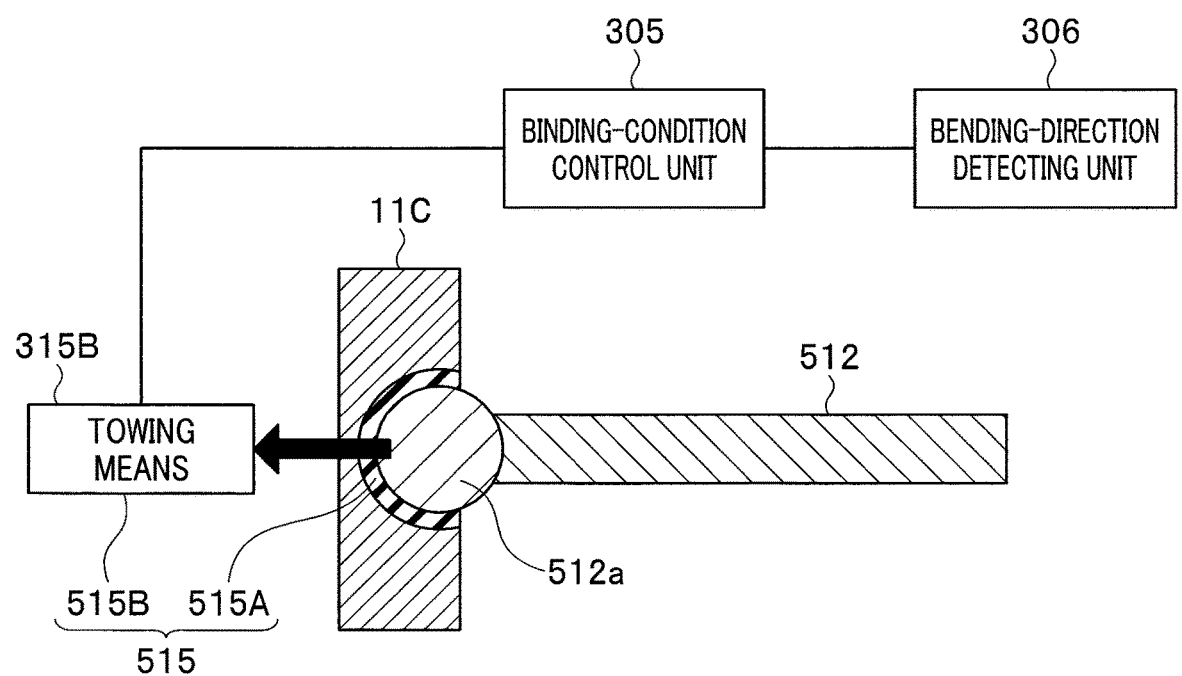
FIG. 19 is a side sectional view showing a schematic configuration of a flexible tube insertion apparatus in a fifth embodiment of the present invention.

FIG. 19 is a side sectional view showing a schematic configuration of the flexible tube insertion apparatus in the fifth embodiment of the present invention.

As shown in FIG. 19, in the fifth embodiment, like the rigidity variable unit 112 in the first embodiment, a rigidity variable unit 512 is configured as a not-shown actuator including a coil heater and a shape memory member and is provided in the longitudinal direction of the insertion section 11 in the predetermined range from the proximal end portion of the bending portion 11B and the distal end portion of the flexible tube portion 11C.

As in the first embodiment, the rigidity variable unit 512 is disposed in the "offset position" separated by the approximate radius r from the center axis in the substantial U direction (the direction separated at the slight angle θ=α from the U direction) in the cross section orthogonal to the longitudinal direction of the insertion section 11 (see FIG. 5).

Further, as in the first embodiment, variable control of rigidity of the rigidity variable unit 512 is performed by the rigidity control unit 302 and, under the control by the control unit 303, bending rigidity of the rigidity variable unit 512 is controlled by a binding unit 515 (an elastic layer 515A and a towing apparatus 515B) controlled by the binding-condition control unit 305.

In the fifth embodiment, an end face of a bound section 512a, which is an end point of the rigidity variable unit 512, is formed in a shape assuming a substantially spherical surface. The bound section 512a is disposed to be in contact with, via the elastic layer 515A explained below, a recess formed at the distal end portion of the flexible tube portion 11C in a boundary portion between the bending portion 11B and the flexible tube portion 11C of the insertion section 11.

On the other hand, in the fifth embodiment, the binding unit 515 is configured by the elastic layer 515A stuck to a recessed surface in the recess formed at the distal end portion of the flexible tube portion 11C and the towing apparatus 515B that tows the bound section 512a in a distal end direction across the elastic layer 515A.

In other words, in the fifth embodiment, the bound section 512a, which is the end point of the rigidity variable unit 512, is towed in the distal end direction by the towing apparatus 515B across the elastic layer 515A in the recess formed at the distal end portion of the flexible tube portion 11C. Therefore, the bound section 512a is pressed by the elastic layer 515A in the binding unit 515. The bound section 512a is bound by the elastic layer 515A pressed by the bound section 512a.

Magnitude of a pressing force of the bound section 512a to the elastic layer 515A in the binding unit 515 is displaced by a towing force of the towing apparatus 515B. For example, the pressing force increases if the towing force of the towing apparatus 515B is large. The pressing force decreases if the towing force of the towing apparatus 515B is small.

Further, the towing apparatus 515B in the binding unit 515 is connected to the binding-condition control unit 305 as in the first embodiment. The towing force is controlled according to the binding condition calculated by the binding-condition control unit 305.

A pressing force (a binding force) received by the bound section 512a from the elastic layer 515A also changes according to magnitude of the towing force of the towing apparatus 515B controlled by the binding-condition control unit 305.

A "pressing force" generated on a contact surface of the bound section 512a with the elastic layer 515A changes, whereby, as in the first embodiment, bending rigidity in the bound section 512a also changes. The bending rigidity of the bound section 512a, which is the end point of the rigidity variable unit 512 extended in the longitudinal direction, changes, whereby, as a result, "apparent bending rigidity" of the rigidity variable unit 512 itself also changes.

<Action in the Fifth Embodiment>

In the fifth embodiment, rigidity control for the rigidity variable unit 512 by the towing apparatus 515B (the binding unit 515) controlled by the binding-condition control unit 305 is the same as the rigidity control in the first embodiment explained above (see, for example, FIG. 7 and FIG. 8). Therefore, detailed explanation about the rigidity control is omitted. In the fifth embodiment, the binding-condition control unit 305 calculates a "binding condition" based on the same rigidity target value as the rigidity target value in the first embodiment and controls the towing apparatus 515B (the binding unit 515).

A "pressing force" corresponding to the target value is applied to the bound section 512a according to the displacement of the towing force of the towing apparatus 515B. Consequently, the binding force of the bound section 512a by the elastic layer 515A (the binding unit 515) also increases. The bending rigidity relating to the bound section 512a also increases.

In this way, in the fifth embodiment as well, the bending rigidity of the bound section 512a, which is the end point of the rigidity variable unit 512, increases, whereby the "apparent bending rigidity" of the rigidity variable unit 512 itself also increases.

The "apparent bending rigidity" of the rigidity variable unit 512 increases, whereby rigidity near the distal end portion of the insertion section 11 (in the range from the proximal end portion of the bending portion 11B to the distal end portion of the flexible tube portion 11C) also increases. By properly setting the target value calculation map, in the case of the large intestine endoscope in the present embodiment, it is possible to suppress fluctuation in a force applied to an intestinal wall of a large intestine and a propulsion force of the insertion section distal end portion.

In other words, in the fifth embodiment, as in the first embodiment, irrespective of a bending direction of the insertion section 11, it is possible to make a load to the intestinal wall of the large intestine uniform and keep the propulsion force of the insertion section 11 constant. Consequently, it is possible to improve insertability of the insertion section 11 while reducing a burden on a subject.

Sixth Embodiment

A sixth embodiment of the present invention is explained.

In the flexible tube insertion apparatus in the first to fifth embodiments, the bound section, which is the end point of the rigidity variable unit, is bound by the binding unit in one place and the bending rigidity of the bound section is controlled. However, a flexible tube insertion apparatus in the sixth embodiment is characterized in that an intermediate binding unit is provided in a part other than the end point of the rigidity variable unit.

Since the other components are the same as the components in the first embodiment, only differences from the first embodiment are explained. Explanation about common portions is omitted.

Figure 20:
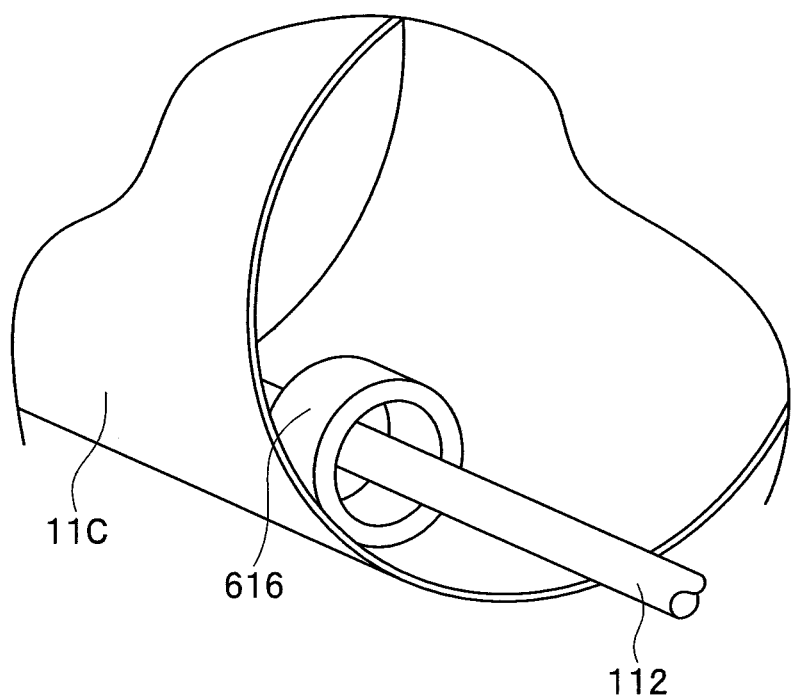
FIG. 20 is a main part enlarged perspective view showing an intermediate binding unit in a flexible tube insertion apparatus in a sixth embodiment of the present invention.
Figure 21:
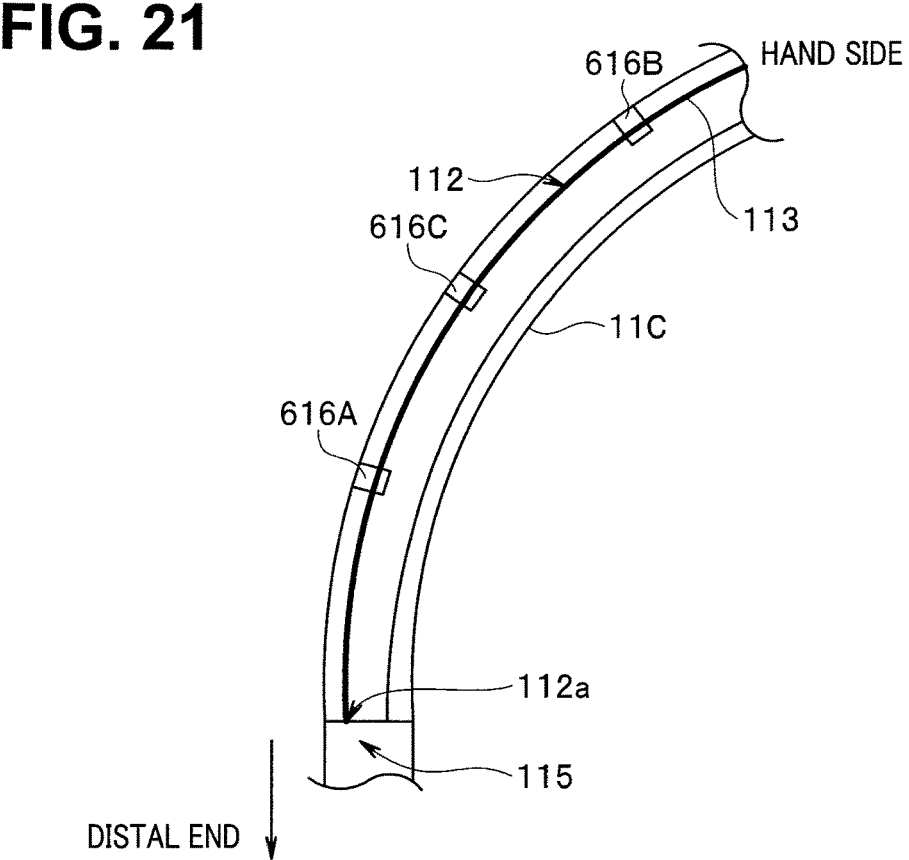
FIG. 21 is a main part enlarged view showing an example in which there are three intermediate binding units in the flexible tube insertion apparatus in the sixth embodiment.
Figure 22:
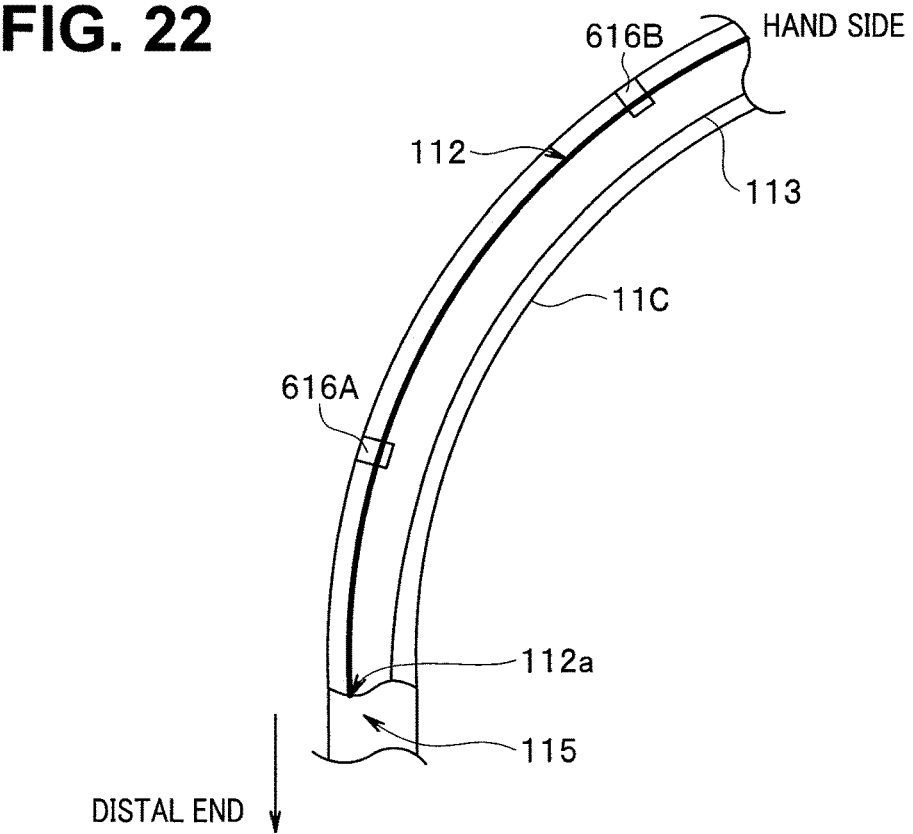
FIG. 22 is a main part enlarged view showing an example in which there are two intermediate binding units in the flexible tube insertion apparatus in the sixth embodiment.

FIG. 20 is a main part enlarged perspective view showing the intermediate binding unit in the flexible tube insertion apparatus in the sixth embodiment of the present invention. FIG. 21 is a main part enlarged view showing an example in which there are three intermediate binding units in the flexible tube insertion apparatus in the sixth embodiment. FIG. 22 is a main part enlarged view showing an example in which there are two intermediate binding units in the flexible tube insertion apparatus in the sixth embodiment.

In the sixth embodiment, in intermediate portions of the rigidity variable unit 112 extended in the longitudinal direction in the insertion section 11, for example, as shown in FIG. 21, in three intermediate portions of the rigidity variable unit 112, intermediate binding units 616A, 616B, and 616C that restrict movement in a radial direction of the rigidity variable unit 112 are respectively provided.

The intermediate binding units 616A, 616B, and 616C are configured by a small-diameter annular member fixed to the inner circumferential surface of the insertion section 11, more specifically, as indicated by a sign 616 in FIG. 20. The rigidity variable unit 112 is insertable movably in an axial direction in an inner diameter portion of the intermediate binding unit 616 configured by the annular member and is movable in a radial direction as well in a range of an inner diameter of the annular member.

In other words, the intermediate binding unit 616 allows extremely slight movement in the radial direction of the rigidity variable unit 112 in the range of the inner diameter of the small-diameter annular member and, on the other hand, plays a function of restricting movement in the radial direction in the inner diameter portion of the insertion section 11.

The example shown in FIG. 21 shows an example in which the intermediate binding unit 616 is disposed in three parts (the intermediate binding units 616A, 616B, and 616C) in the intermediate portions in the rigidity variable unit 112. The example shown in FIG. 22 shows an example in which the intermediate binding unit 616 is disposed in two parts (the intermediate binding units 616A and 616B) in the intermediate portions in the rigidity variable unit 112.

Note that, as explained above, in the sixth embodiment, the example is explained in which the intermediate binding unit 616 is disposed in the three parts or the two parts. However, not only this, but, naturally, the intermediate binding unit 616 may be provided in one part or four or more parts.

According to the sixth embodiment, when the bending rigidity of the rigidity variable unit 112 itself is controlled by the bending rigidity control in the bound section 112a, which is the end point of the rigidity variable unit 112, it is possible to prevent the rigidity variable unit 112 to be hardened from carelessly moving in the radial direction of the insertion section 11. It is possible to make surer the effect of the bending rigidity control for the rigidity variable unit 112 and further improve the insertability of the insertion section 11.

The present invention is not limited to the embodiments explained above. Various changes, alterations, and the like are possible within a range not changing the gist of the invention.

What is claimed is:

1. A flexible tube insertion apparatus comprising:
    an insertion section;
    a variable rigidity actuator disposed in a first position deviating from a center axis of the insertion section in a center axis direction of the insertion section, the variable rigidity actuator and configured to change rigidity of the insertion section; and
    a variable pressing force actuator configured to bind a proximal end portion of the variable rigidity actuator, the variable pressing force actuator configured to change a pressing force applied to an outer circumferential surface of the proximal end portion; and
    a processor configured to control the variable pressing force actuator such that rigidity in the variable rigidity actuator is lower when a bending direction of the insertion section is a direction approaching the first position from the center axis than when the bending direction of the insertion section is a direction away from the first position.

2. The flexible tube insertion apparatus according to claim 1, wherein the variable rigidity actuator is an elongated shape memory alloy.

3. The flexible tube insertion apparatus according to claim 1, wherein the variable pressing force actuator is configured by a plurality of plate-like members configured by a shape memory alloy.

4. The flexible tube insertion apparatus according to claim 1, wherein the variable pressing force actuator is configured by a balloon.

5. The flexible tube insertion apparatus according to claim 1, wherein
- a proximal end of the variable rigidity actuator is formed in a spherical shape and disposed in a recess formed in the insertion section, and
- the variable pressing force actuator includes a towing apparatus that tows the proximal end portion in a distal end direction of the insertion section across an elastic layer provided in the recess.

6. The flexible tube insertion apparatus according to claim 1, wherein the proximal end portion of the variable rigidity actuator is a proximal end portion of a distal end part of the insertion section.

\* \* \* \* \*